United States Patent [19]

Osten et al.

[11] Patent Number: 5,706,208

[45] Date of Patent: Jan. 6, 1998

[54] METHOD FOR THE PREDICTION OF PROPERTIES OF BIOLOGICAL MATTER BY ANALYSIS OF THE NEAR-INFRARED SPECTRUM THEREOF

[75] Inventors: David W. Osten, Grant Township, Minn.; James B. Callis, Seattle, Wash.

[73] Assignees: Minnesota Mining And Manufacturing Company, St. Paul, Minn.; The Board of Regents of The University of Washington, Seattle, Wash.

[21] Appl. No.: 995,543

[22] Filed: Dec. 22, 1992

Related U.S. Application Data

[63] Continuation of Ser. No. 408,746, Sep. 18, 1989, abandoned.

[51] Int. Cl.$^6$ ............................................. G06F 159/00
[52] U.S. Cl. ........................................................ 364/497
[58] Field of Search ................................... 364/497–499, 364/413.07, 413.08, 413.09; 356/39, 40; 128/633, 635; 250/338.1, 338.5, 340, 341, 343

[56] References Cited

U.S. PATENT DOCUMENTS

| | | | |
|---|---|---|---|
| 3,648,160 | 3/1972 | Beaver | 324/30 B |
| 3,877,818 | 4/1975 | Button et al. | 356/186 |
| 4,017,192 | 4/1977 | Rosenthal | 356/39 X |
| 4,086,915 | 5/1978 | Kofsky et al. | 128/2 L |
| 4,114,604 | 9/1978 | Shaw et al. | 128/2 L |
| 4,210,809 | 7/1980 | Pelavin | 250/343 |
| 4,223,680 | 9/1980 | Jöbsis | 128/633 |
| 4,243,883 | 1/1981 | Schwarzmann | 250/343 |
| 4,281,645 | 8/1981 | Jöbsis | 128/633 |
| 4,303,336 | 12/1981 | Cullis | 356/39 |
| 4,345,150 | 8/1982 | Tamura et al. | 250/339 |
| 4,407,290 | 10/1983 | Wilber | 128/633 |
| 4,427,889 | 1/1984 | Müller | 250/339 |
| 4,447,150 | 5/1984 | Heinemann | 356/41 |
| 4,466,076 | 8/1984 | Rosenthal | 364/571 |
| 4,485,820 | 12/1984 | Flower | 128/633 |
| 4,523,279 | 6/1985 | Sperinde et al. | 364/416 |
| 4,586,513 | 5/1986 | Hamaguri | 128/633 |
| 4,633,087 | 12/1986 | Rosenthal et al. | 250/341 |

(List continued on next page.)

FOREIGN PATENT DOCUMENTS

| | | |
|---|---|---|
| 0240742 | 6/1987 | European Pat. Off. . |
| WO 90/04353 | 5/1990 | WIPO . |
| WO 90/04941 | 5/1990 | WIPO . |

OTHER PUBLICATIONS

Stark, E., and Luchter, K., "Near–Infrared Analysis (NIRA): A Technology for Quantitative and Qualitative Analysis," *Applied Spectroscopy Reviews*, 22(4):335–399 (1986).

(List continued on next page.)

*Primary Examiner*—Gail O. Hayes
*Assistant Examiner*—David Huntley
*Attorney, Agent, or Firm*—Gary L. Griswold; Walter N. Kirn; John H. Hornickel

[57] ABSTRACT

A method for predicting a property of a matter of biological origin, such as biological fluid, containing water, where the biological matter may be approximated to contain two compartments where one compartment has a proportionally larger or smaller amount of water than the other compartment having the property of interest. The method establishes a training set in the near-infrared (NIR) region with independent quantification of the property of the matter using known techniques. The training set is mathematically analyzed according to a correlation developed by regression analysis after employment of a ratio pre-processing technique. The result is a mathematical transformation equation which quantitatively relates spectral intensities at specific wavelengths to the property of interest. This transformation equation may be applied to unknown samples so as to predict their properties, thereby eliminating need for the reference method except for validation or recalibration. There is rapid and accurate prediction of the property of the unknown sample, which may be the property of hematocrit or hemoglobin concentration in whole animal blood.

20 Claims, 5 Drawing Sheets

U.S. PATENT DOCUMENTS

| | | | |
|---|---|---|---|
| 4,642,778 | 2/1987 | Hieftje et al. | 364/498 |
| 4,651,741 | 3/1987 | Passafaro | 128/633 |
| 4,655,225 | 4/1987 | Dahne et al. | 128/633 |
| 4,660,151 | 4/1987 | Chipman et al. | 364/498 |
| 4,701,838 | 10/1987 | Swinkels et al. | 364/164 |
| 4,745,279 | 5/1988 | Karkar et al. | 250/343 |
| 4,800,279 | 1/1989 | Hieftje et al. | 250/339 |
| 4,805,623 | 2/1989 | Jöbsis | 128/633 |
| 4,825,076 | 4/1989 | Shields | 250/343 |
| 4,935,875 | 6/1990 | Shah et al. | 364/497 |
| 4,958,295 | 9/1990 | Davidson et al. | 364/497 |
| 4,972,331 | 11/1990 | Chance | 364/550 |
| 4,975,581 | 12/1990 | Robinson et al. | 364/498 |

OTHER PUBLICATIONS

Ciurczak, E.W., "Uses of Near–Infrared Spectroscopy in Pharmaceutical Analysis," *Applied Spectroscopy Reviews*, 23(1&2):147–163 (1987).

Wetzel, D.L., "Near–Infrared Reflectance Analysis: Sleeper Among Spectroscopic Techniques," *Analytical Chemistry*, 55(12):1165–1176 (Oct. 1983).

Wyatt, J.S., Delpy, D.T., Cope, M., Wray, S., and Reynolds, E.O.R., "Quantification of Cerebral Oxygenation and Haemodynamics in Sick Newborn Infants by Near Infrared Spectrophotometry," *The Lancet*, 1063–1066 (Nov. 8, 1986).

Osborne, B.G., and Fearn, T., "Technical Note: Discriminant Analysis of Black Tea By Near Infrared Reflectance Spectroscopy," *Food Chemistry*, 29:233–238 (1988).

Lum et al., "Evaluation of Pulse Oximetry With EKG Synchronization," IEEE Engineering in Medicine & Biology Society 10th Annual International Conference, Copyright 1988.

Lee et al., "Measurement of Percent Carboxyhemoglobin With Pulse–Oximetry Technique," IEEE Engineering in Medicine & Biology Society 10th Annual International Conference, Copyright 1988.

Dickensheets et al., "Pathlength Independent Spectrophotometric Measurement of Hemoglobin in Solution," IEEE Engineering in Medicine & Biology Society 11th Annual International Conference, published Nov. 1989.

Lee et al., "Simultaneous Measurement of Percent Carboxyhemoglobin and Functional Oxygen Saturation," IEEE Engineering in Medicine & Biology Society 11th Annual International Conference, published Nov. 1989.

Dickensheets, "A Study of Non–Invasive Quantitative Estimation of Circulating Bilirubin in Newborns," Masters Thesis University of Washington, Chapters II–V, published Mar. 3, 1989.

Chance et al., "Time–Resolved Spectroscopy of Hemoglobin and Myoglobin in Resting and Ischemic Muscle", *Analytical Biochemistry* 174, pp. 698–707 (1988).

M. Nyden et al., "Spectroscopic Quantitative Analysis", *Applied Spectroscopy*, vol. 42, No. 4, pp. 588–594, Apr. 1, 1988.

H. Kisner et al., "Multiple Analytical Frequencies and Standards", *Analytical Chemistry*, vol. 55, No. 11, pp. 1703–1707, Sep. 1, 1983.

P. Geladi et al., "Linearization and Scatter Correction for Near Infrared", *Applied Spectroscopy*, vol. 39, No. 3, pp. 491–500, Jul. 1, 1985.

G. Janatsch et al., "Multivariate Calibration for Assays in Clinical Chemistry", *Analytical Chemistry*, vol. 61, No. 18, pp. 2016–2023, Sep. 15, 1989.

H. Martens et al., "Multivariate calibration", *TRAC: Trends in Analytical Chemistry*, vol. 3, No. 8, pp. 204–210, Sep. 1, 1984.

M. Josefson et al., "Optical Fiber Spectrometry", *Analytical Chemistry*, vol. 60, No. 24, pp. 2666–2671, Dec. 15, 1988.

Barlow et al., "Absorption Measurements for Oxygenated and Reduced Hemoglobin in the Range 0.6–1.88 Microns", *Clinical Chemistry*, vol. 8, No. 1 (1962).

A. Van Toorenenbergen et al., "Measurement of Total Serum Protein", *Journal of Clinical Chemistry & Clinical Biochemistry*, vol. 26, No. 4, pp. 290–211, Jul. 1, 1988.

R. Looder et al., "Assessment of the Feasibility of Determination of Blood Constituents", *Talanta*, vol. 36, No. 1, pp. 193–198, Mar. 1, 1989.

E. Peuchant et al., "Determination of Serum Cholesterol", *Analytical Chemistry*, vol. 59, No. 14, pp. 1816–1819, Jul. 15, 1987.

P. Robert et al., "Multivariate Analysis", *Analytical Chemistry*, vol. 59, No. 17, pp. 2187–2191, Sep. 1, 1987.

"Noninvasive Determination of Hemoglobin Saturation in Dogs by Derivative Near–infrared Spectroscopy", *American Physiological Society*, Ferrari et al., 1989, pp. H1493–1499.

"Reflectance Measurements of Hematocrit and Oxyhemoglobin Saturation", *American Physiology Society*, Steinke et al., Jul., 1987, pp. H147–153.

"Review: Infrared Spectrometry", *Anal. Chem.*, (McDonald), 1986, pp. 1906–1925.

"Focus Near–Infrared Spectrometry in Clinical Analysis", *Anal. Chem.*, Anon., Jul., 1986, pp. 874, 876.

"A Comparative Study of Two Computerized Spectrophotometers for the Near–Infrared Analysis of Wheat for Protein", *Applied Spectroscopy*, 1986, Williams et al., pp. 785–790.

"Salinity Determination Using NIRA", Hirschfeld, *Appl. Spectrosc.* 1985, 39(4), 7400–741.

"Near Infrared Analysis", *Analytical Instrumentation*, Honigs, 1985, pp. 1–62.

"Near–Infrared Determination of Several Physical Properties of Hydrocarbons", *Anal. Chem.*, vol. 57, No. 2, Honigs et al., Feb., 1985, pp. 443–445.

"A New Method for Obtaining Individual Component Spectra from Those of Complex Mixtures", *Appl. Spectroscopy*, vol. 38, No. 3, Honigs et al., 1984, pp. 317–322.

"Multicomponent Quantitative Analysis", *Appl. Spectroscopy Reviews*, Brown and Obremski, 1984, pp. 373–418.

"Predicting Forage Quality by Infrared Reflectance Spectroscopy", *Journal of Animal Science*, vol. 43, No. 4, Norris et al., 1976, pp. 889–897.

"Compscan Systems Operator's Manual, vol. I—Instruction Manual", Pacific Scientific Company, Caseiero et al., 1985, pp. 6–12, 29–185.

METHOD FOR THE PREDICTION OF PROPERTIES OF BIOLOGICAL MATTER BY ANALYSIS OF THE NEAR-INFRARED SPECTRUM THEREOF

This is a continuation of application Ser. No. 07/408,746 filed Sept. 18, 1989, now abandoned.

FIELD OF THE INVENTION

The present invention relates to the analysis of a sample of matter of biological origin using the near-infrared (NIR) spectrum of that biological matter having a water content. The method permits prediction of a property of interest because the biological matter may be approximated to contain two compartments where one compartment has a proportionally larger or smaller amount of water than the other compartment having the property of interest. Analysis of an unknown sample is achieved by use of mathematical techniques developed using a NIR spectral training set of known samples and independent quantification of the property of interest in the known samples in that training set.

This invention was made with Government support under PATH/HEALTHTECH contract number 88-0256. The Government has certain rights in this invention.

BACKGROUND OF THE INVENTION

Presence of water in an organism is the common denominator of life. The corpus of an organism is compartmentalized with each compartment capable of being distinguished by the amount of water it contains. The processes of osmosis and reverse osmosis in an organism act to stabilize this compartmentalization.

Determination of the volume fraction or percentage concentration of components other than water in the various compartments of biological matter, such as tissue or blood, is often critical to the determination of the well-being or homeostasis of the organism. Whether in the botanical, medical, zoological or veterinary arts, because the circulation of biological fluid or existence of certain biological tissue in an organism is necessary for life, the diagnosis of such biological matter provides an excellent medium to assess the homeostatic condition of the organism.

Blood of animals circulates essential nutrients of life. Erythrocytes, red blood cells, flowing in the blood plasma carry oxygen to all other cells of the organism. Hematocrit is the volume fraction of agglomerated erythrocytes in whole blood. Hemoglobin is the chemical molecule in the erythrocytes which transports oxygen to the cells. Hemoglobin may take several forms depending on the presence or absence of oxygen or other chemicals which may be bonded to active sites in the hemoglobin molecule. Hematocrit in whole blood has been found to have a suitable direct mathematical correlation to the concentration of hemoglobin, providing the blood has few or no lysed erythrocytes.

Water is omnipresent in whole blood. Hemoglobin is dissolved in the erythrocytes, while plasma is principally water. But the amount of water in which hemoglobin is dissolved, and hence in erythrocytes, is comparatively less than the amount of water in the plasma.

Clinical analysis of an organism requires monitoring of the status of or the changes in condition. As a result of injury or illness or other deleterious biological conditions, the hematocrit or the concentration of hemoglobin in erythrocytes available for oxygen transport to the cells of the organism may be diminished below healthy levels even to the point of critical life sustaining levels. Also, analysis of various types of anemia is vital to continuing successful treatment of a patient, especially in critical care facilities such as emergency rooms, operating rooms, or intensive care units, including neo-natal units. Less traumatic but just as vital, most blood donors must undergo hematocrit testing to assure that their blood to be donated has appropriate hemoglobin levels for later use.

Several types of techniques have been known for the analysis of blood during patient care. Hemoglobin concentrations are measured traditionally using lengthy and complicated procedures which require the preconditioning, i.e., chemical modification or component separation, of a blood sample withdrawn from the body. These traditional methods destroy the blood, preventing its return to the body.

One popular method for the determination of hemoglobin involves (1) lysing the red blood cells by hypotonic shock or sonification, (2) removal of the red blood cell membranes to produce a clear solution, (3) addition of a cyanide ion reagent to normalize or convert the various forms of hemoglobin to a single form hemoglobin (e.g., cyanomet hemoglobin), and (4) spectrophotometric analysis to derive the hemoglobin concentration of the normalized sample.

Because of the complicated chemical procedure for determination of hemoglobin concentration, and because of the known direct correlation between hematocrit and hemoglobin concentration, methods for independently determining hematocrit have been developed.

The most common methods for measurement of hematocrit can be divided into two categories: centrifugal attribution in a test tube of specific diameter and Coulter counting.

Centrifugal attribution involves centrifuging of blood withdrawn from the body in a tube of specific diameter at pre-selected centrifugal forces and times that serve to separate the blood into two portions. The heavier portion is the agglomeration of erythrocytes in the whole blood. The lighter portion is plasma dominated by water. The ratio of the volume of the erythrocytes to the total volume of the blood sample in the centrifuge tube is the hematocrit.

Coulter counting determines hematocrit by physical counting of red blood cells and a determination, through the size of each cell on a cell-by-cell basis, the volume of each. After a predetermined number of blood cells are counted, the hematocrit is determined by the number of red blood cells counted multiplied by the mean volume of the blood cells for a given blood sample.

As may be understood by considering such current methods, considerable manipulation and laboratory analysis is necessary for each individual blood sample drawn from the body of the patient. Whether measuring hematocrit or hemoglobin concentration, the blood sample is withdrawn from the patient and inevitably taken from the immediate vicinity of the patient for analysis using expensive, stationary instrumentations that require preconditioning of the sample in order to analyze it.

Efforts to spectrally analyze blood samples for hematocrit or hemoglobin concentration have been attempted. U.S. Pat. 4,243,883 describes a monitor of a flowing stream of blood using a discrete near-infrared wavelength. U.S. Pat. 4,745,279 describes a dual path NIR spectral analysis at discrete wavelengths of flowing whole blood. U.S. Pat. 4,805,623 describes a NIR spectral method and apparatus using multiple wavelengths to determine the concentration of a dilute component of known identity in comparison with a reference component of known concentration.

The near-infrared (NIR) spectral region of electromagnetic radiation, from about 680 nanometers to 2700 nanometers, contains absorbance peaks for the various forms of hemoglobin and water. Prior spectral analytical efforts have focused on the measurement of the diffuse transmission or reflectance of near infrared light through blood samples. However, light scattering in the samples and other properties which interfere with accurate measurement cause variances in the specific spectrum taken. As a result, even using measurements taken with sensitive instrumentation is not satisfactory. Moreover, the choice of specific wavelengths in near-infrared spectra for which whole blood samples may be best monitored is not straightforward due to variances in the broad peaks of water and various forms of hemoglobin in such NIR spectra.

Even with the best monitoring wavelengths being chosen, one must address the variability caused by the effective path length that the transmitted or reflected near-infrared radiation takes between excitation and detection through the blood sampling. Prior efforts to employ NIR spectral analysis have either discounted the importance of determining effective path length or required procedures to establish the effective path length prior to completing the spectral analysis. In the former case, reproducible precision suffers; in the latter case, a complicated methodology is employed.

Thus, what is needed is a method for accurately determining through NIR spectral analysis a property of a sample of biological matter which is rapid, inexpensive, accurate, precise, and which takes into account such spectroscopic variabilities as effective path length of the reflected or transmitted light or where instrumentation may be using either a continuous detection or measurement of absorbance wavelengths across a NIR spectra or at discrete wavelengths thereof.

SUMMARY OF THE INVENTION

The present invention provides a method for rapidly, inexpensively, and accurately characterizing the properties of matter of biological origin containing water by analyzing the near-infrared spectrum of the biological matter using techniques useful with NIR spectral instrumentation and predicting the properties without sample preconditioning. The techniques seek the best ratio of spectrally analyzed wavelengths and use mathematical regression analysis to permit transforming the observed spectrum into a prediction of the property to be analyzed.

The method of the present invention avoids chemical alteration or physical separation of the components in the sample of biological matter. The method also avoids inaccuracies caused by irrelevant variations in samples and instrumental noise in measurement techniques.

The method of the present invention is founded on the principle that the biological matter may be considered to consist of essentially two compartments: one compartment which has a proportionally different (larger or smaller) amount of water than the other compartment related to or having the property to be analyzed. The present invention is also founded on the principle that identification of the volume or weight fraction or concentration of water in the biological matter will serve as the basis for calculation of the property to be analyzed. The method of the present invention is further founded on the principle that the establishment of a training set of the combination of NIR spectra of several samples of the biological matter and the independent quantification of the property to be analyzed in each sample provides a source of mathematical comparison for accurately predicting the property to be analyzed in an unknown additional sample by using such mathematical comparison.

When the biological matter is whole blood, prediction of the hematocrit or hemoglobin concentration is achieved by obtaining near-infrared spectra of a statistically sufficient number of samples of whole blood to establish a training set for mathematical comparisons against individual additional unknown samples of other whole blood. Further, the property to be analyzed in the whole blood, e.g., hematocrit or hemoglobin concentration, is independently quantified by using an independent known technique: lysing and chemical alteration for hemoglobin and Coulter counting or centrifuging for hematocrit.

Having established a training set of NIR spectra and independently quantified the hematocrit or hemoglobin concentration in each sample in the training set, the nature of the inter-relationship between the hematocrit or hemoglobin and the water content is statistically correlated to establish the source of comparison when predicting unknown samples.

To minimize variability when establishing the training set and when predicting the properties of the compartment being analyzed in the unknown sample, a ratio pre-processing technique against the spectra detected is employed.

The ratio pre-processing technique of the present invention utilizes a ratio of the absorbance peak of water in the biological fluid to another NIR spectral absorbance measuring point identified by mathematical regression analysis as providing a mathematical correlation to accurately predict the property of the compartment being analyzed in the unknown sample.

In the case of hematocrit or hemoglobin concentration determinations, through mathematical regression analysis, it has been found that use of the absorbance peak of water appearing in NIR spectra in the range of from about 1150 to about 1190 nanometers (nm) provides an accurate and reproducible peak for ratio pre-processing techniques, notwithstanding a known decrease in detector efficiency using silicon detectors in this range of wavelengths. This peak of absorbance of water in the 1150–1190 nm range is largely isolated from the absorbance of hemoglobin either in its oxygenated state or in its deoxygenated state. The absorbance peak of water in this region is primarily the result of simultaneous excitation of the symmetric O—H stretch, the O—H bending mode, and the antisymmetric O—H stretch of the water molecule, whether existing in the biological matter as free water, bound to other molecules, or other forms.

Through mathematical regression analysis, the other absorbance measuring point has been found to be in the range from about 780 to about 830 nm where the extinction coefficients of oxyhemoglobin and deoxyhemoglobin are equivalent, also known as the isosbestic point.

The use of ratio of these two wavelengths to minimize the effects of light scattering and instrumental noise also has physical significance for prediction of hematocrit and hemoglobin concentration. The ratio emulates the ratio used to value hematocrit: erthrocyte solids over total volume of plasma and erthrocytes. The ratio also emulates the concentration of hemoglobin, which is expressed in grams per deciliter of water: hemoglobin absorbance per water absorbance.

Obtaining the training set spectral data for the samples of the biological matter depends on the type of instrumentation to be employed. To establish the training set for this invention, the biological matter is withdrawn from the body of the organism.

For purposes of full disclosure it is known that the biological matter need not be withdrawn, such as disclosed in U.S. patent application Ser. No. 408,890 filed concurrently by the applicants and another, which disclosure is adopted and incorporated herein by reference for purposes of full disclosure.

However, to provide the independent quantification of the property to be analyzed from the training set samples, a sample of the biological matter must be withdrawn from the organism and often cannot be returned to the organism because of chemical alteration or physical separation.

Gathering the unknown sample spectral data for analysis also depends on the type of instrumentation to be employed. In an embodiment of the present invention, the unknown sample is withdrawn in the same manner as the samples of the biological matter comprising the training set.

Processing and instrumentation variabilities are dependent upon the method by which the training set is established and the method by which the unknown sample is analyzed. In the case of in vitro (NIR) spectral analysis, the biological fluid is stationary when being spectrally analyzed, a static condition.

When the biological fluid is whole blood and the hematocrit or the concentration of hemoglobin is desired, after the training set is established and the ratio pre-processing technique has been used to minimize sample and instrumentation variability, a sample of whole blood is withdrawn from a patient and spectrally analyzed in a stationary configuration either using transmission detection or reflectance detection. However, the method of detection employed must be the same for both the establishment of the training set and the investigation of the unknown sample. Because of the use of the ratio pre-processing technique, variations due to sampling techniques and instrumentation factors such as effective path length are minimized.

The NIR spectrum of the unknown sample is obtained from either continuous or discrete wavelength measuring instrumentation. After the spectrum is obtained and subjected to the ratio pre-processing, the property of interest may be predicted by a mathematical correlation to the training set spectra.

In the case of the measurement of hematocrit or hemoglobin concentration in an unknown sample of whole blood, after the NIR spectrum of the unknown sample is obtained and subjected to ratio pre-processing, application of mathematical techniques comparing the training set data for the hematocrit or the hemoglobin concentration with the unknown sample's spectra allows prediction of the hematocrit or the hemoglobin concentration in the unknown sample.

For an additional appreciation of the scope of the present invention, a more detailed description of the invention follows, with reference to the drawings.

EMBODIMENTS OF THE INVENTION

One embodiment of the present invention is the analysis of hematocrit in whole blood. Another embodiment of the present invention is the analysis of hemoglobin concentration in whole blood. There are occasions when either analysis may be preferred. But generally, it is recognized that the determination of hematocrit is an excellent correlation to the concentration of hemoglobin in whole blood. However for versatility of the system, it should be recognized that one or more methods of independent quantification of the property to be analyzed may be used to provide alternative clinical diagnosis of the condition of the patient.

It should also be recognized that the property of the biological matter to be analyzed must have some correlation either positively or negatively with the water content in the biological matter in order to develop a mathematical correlation therefor in accordance with the present invention. That may not preclude the presence of other components in de minimus volume fractions or concentrations. For example, in whole blood, the presence of white blood cells, platelets, hydrocarbonaceous lipids, and the like are not present in sufficient quantity at the desired level of precision to destroy the validity of the mathematical correlation found.

Figure 1:
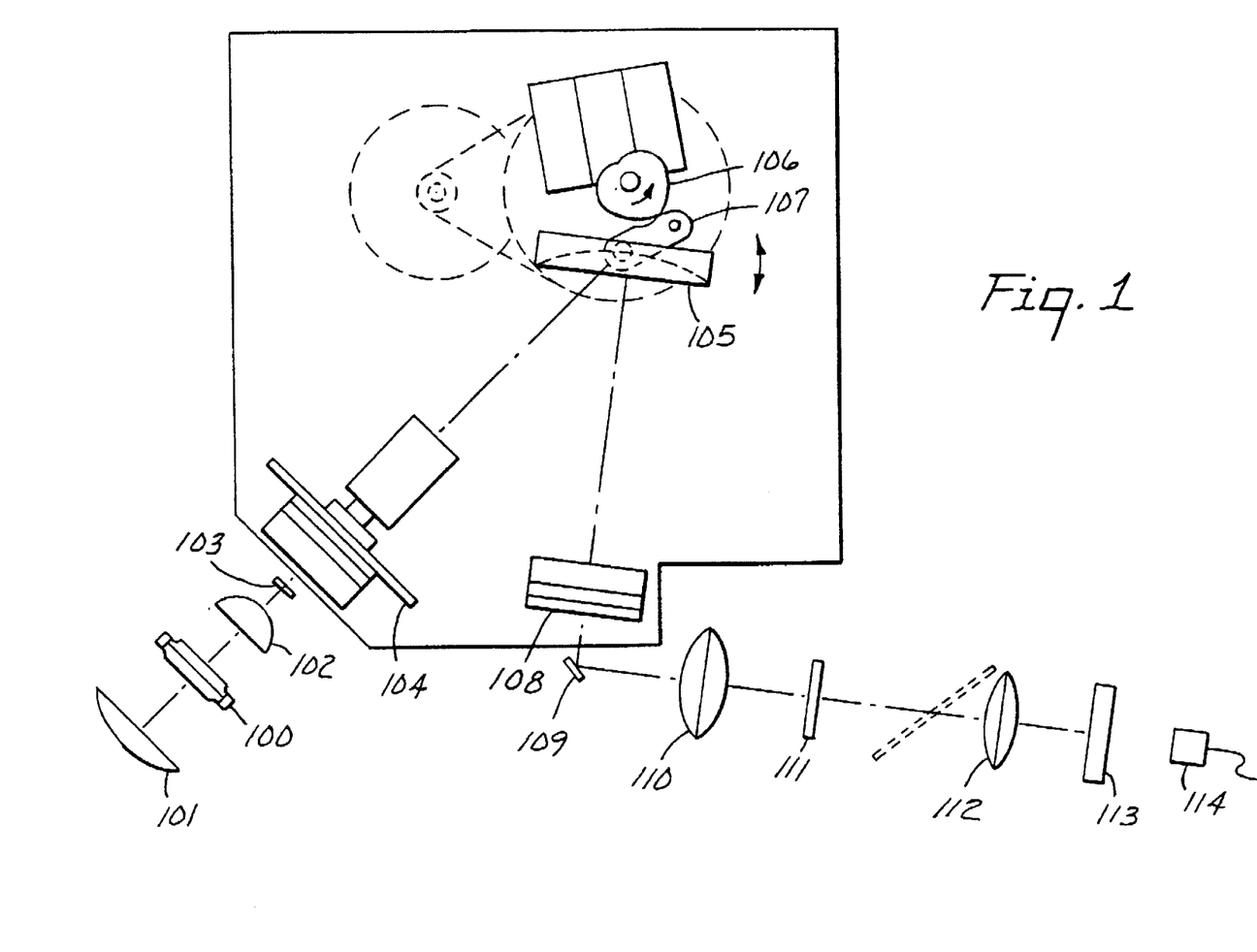
FIG. 1 is a schematic block diagram of the instrumentation useful in a method carried out in accordance with the present invention.

FIG. 1 identifies the schematic block diagram of spectral instrumentation useful in establishing the training set initially and thereafter predicting the property of the compartment to be analyzed in one or more unknown additional samples.

FIG. 1 illustrates a typical instrumentation system available which can be used for obtaining the near infrared spectrum of a biological fluid, such as whole blood. Specifically, FIG. 1 identifies a Model 6250 spectrophotometer manufactured by Near Infrared Systems of Silver Spring, Md., formerly known as Model 6250 made by Pacific Scientific. The radiation from a tungsten lamp 100 is concentrated by a reflector 101 and lens 102 on the entrance slit 103 of the monochromator and thereafter passed through an order sorting filter 104 before illuminating a concave holographic grating 105 to disperse the radiation from the tungsten lamp 100 onto the sample 113. The grating 105 is where the wavelength dispersion occurs. The grating is scanned through the desired wavelength range, typically 680 to 1235 nanometers, by the rotating cam bearing 106, which is coupled to the grating by linkage assembly 107. The selected wavelength passes through exit slit 108 and is guided through the sample cuvette 113 by mirror 109, iris 111, and lenses 110 and 112. After passing through the sample, the remaining radiation is converted to an electrical signal by detector 114.

Other types of instrumentation are also acceptable for use with the methods of the present invention. Monochromators such as Model HR 320 available from Instruments S.A. are useful. Polychromators such as the Chemspec Model 100S available from American Holograph or Model JY320 also available from Instruments S.A. may be used to gather the spectral data to establish the training set.

Detection means may employ either diffuse transmittance detection devices or reflectance devices available commercially. The Model 6250 spectrophotometer may be configured to detect either diffuse transmittance or diffuse reflectance. Depending on factors such as cost, wavelength range desired, and the like, the detector 114 may be a silicon detector, a gallium arsenide detector, a lead sulfide detector, an indium gallium arsenide detector, a selenium detector or a germanium detector.

Whichever detector is chosen, it is preferred to be consistent in the usage of same detection means for establishing the training set spectra and for measuring the unknown sample's spectrum.

Alternately, polychromatic analyzers using a reversed beam geometry may be used to disperse the transmitted or reflected light into its spectral components and photodiode arrays may be used to detect or measure the dispersed light at different positions along the output spectral plane.

Other types of array detectors include charge coupled devices, charge injection devices, silicon target vidicons, and the like. Desirably, the polychromatic analyzer should include an entrance slit that defines the bandwidth of light which is consistent with the spectal resolution desired. One commercially available photodiode array useful with the present invention is Model 1024S photodiode array available from Reticon, Inc., which consists of 1024 diodes of 25 micron width and 2.5 millimeters height. That photodiode array may be used in a complete spectral detection system such as Model ST120 available from Princeton Instruments.

One can also use interference filters as spectroanalyzers, for example, by passing a series of discrete wavelength interference filters one at a time before a suitable detector. It is also possible to use interferometers or a Hadamard transform spectrometer to analyze the diffuse light.

The above detection means are based on detection of spectra from a broad band light source. However, if narrow band sources of NIR light are to be used, such as tungsten lamps with interference filters, light emitting diodes, or laser (either a single tunable laser or multiple lasers at fixed frequencies), other detection techniques may be used. For example, the input signal can be multiplexed either in time, (to sequence each wavelength), or in wavelength (using sequences of multiple wavelengths), and thereafter modulated and the collected signals demodulated and demultiplexed to provide individual wavelength signals without the need for optical filtering.

Regardless of the instrumentation selected, it is preferred to use a computer connected to the instrument to receive the spectral data, perform the analytical calculations described below, and provide a printout or readout of the value of the property predicted. When using spectrometric instruments such as the Model 6250 Spectrometer described above, a personal computer such as a "PS/2" Model 50 computer from IBM of Boca Raton, Fla. is used and preferred.

Figure 2:
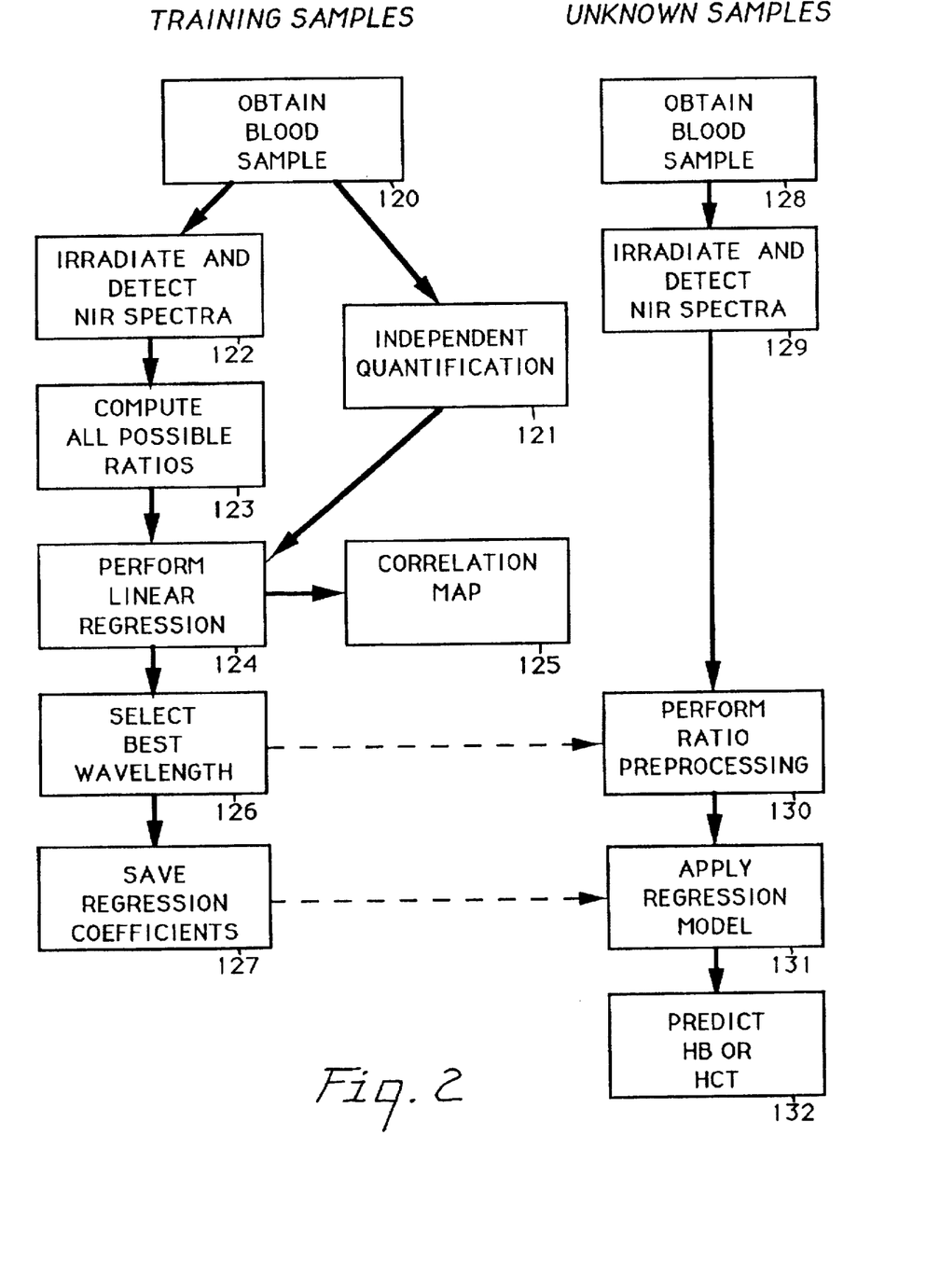
FIG. 2 is a schematic flow chart of the methods to mathematically minimize variability of spectral data and establish the mathematical correlation between known samples and the training set spectra, in order to permit the predicting of the property of interest in an unknown sample by comparison with the mathematical correlation.

FIG. 2 is a schematic flow chart of the ratio preprocessing technique employed to minimize sample and instrumentation variability and the regression analysis to identify the nature of the mathematical correlation between the property to be analyzed in the first compartment and the water content in the biological matter, in order to predict the property to be analyzed in an unknown sample.

The schematic flow of the processing steps involved in determining the property of interest in the biological matter, such as hematocrit or hemoglobin concentration, can be broadly divided into two parts: steps 120 to 127 which comprise the training phase of the analysis and steps 128 to 132 which comprise the prediction of the property of an unknown sample.

The training or calibration development phase consists of obtaining a series of blood samples 120 by withdrawing the samples from one or more animals of the same species. Each training sample is analyzed on two parallel paths.

The first path consists of independent quantification of the property of interest, step 121. It is important that the independent quantification be done accurately. The accuracy of the method of the present invention is dependent upon the accuracy of the independent quantification step 121 because validation of the mathematical correlation is based on the independently quantified value of the property of interest.

The second path consists of irradiating the samples with infrared light and detecting the near infrared spectrum for each sample, step 122, and then computing all possible ratios of two wavelengths in the spectrum, step 123. It should be understood that reference to detecting the near infrared spectrum involves both the measurement of the diffusely transmitted or reflected spectrum and the transformation of that spectrum to an absorbance spectrum. The transformation is based on having taken spectrum of the cell containing only air for calibration purposes.

When the near infrared spectrum has been detected on a Near Infrared Systems model 6250 spectrophotometer, the near infrared spectrum from 680 to 1235 nanometers consists of 700 individual absorbance measurements. The preprocessing step of computing all possible ratios of two wavelengths expands the 700 point spectrum into 700*700 or 490,000 ratio pairs. Since near infrared spectra consist of broad, slowly changing absorbance bands, computing the ratio terms using every fifth data point, 140 point spectrum, results in equivalent performance with a significant decrease in the overall computation requirement, 140*140 or 19,600 ratio terms.

The pre-processed spectra for the set of training samples consisting of the calculated ratios, step 123, are correlated with the values obtained during the independent quantification step 121 by using a mathematical regression technique, step 124, such as linear regression. The pair providing the best correlation of calculated values to actual values is generally the pair of wavelengths chosen for the ratio in the mathematical correlation.

One of the outputs of this regression step is a correlation map, step 125, which graphically shows the regions of the spectrum where the most useful ratio pairs are found. The best ratio pair, step 126, is selected by identifying a region of high correlation which is also independent of small changes in the actual wavelength selected. The regression coefficients corresponding to the selected ratio pair are saved, step 127, for future application to the analysis of individual samples to predict the property of interest.

The steps 128 to 132 in FIG. 2 show the procedure to be followed for predicting hematocrit (abbreviated as HCT in FIG. 2) or hemoglobin (abbreviated as HB in FIG. 2) concentration in an individual unknown sample. A blood sample of unknown hematocrit or hemoglobin concentration, step 128, is obtained and the near infrared spectrum of this sample is detected or measured, step 129.

While the near infrared spectrum of additional unknown samples may also be detected on exactly the same instrument as the training samples were measured and from which the training set is prepared, it is also acceptable to use a simpler instrument which will provide the absorbance at only the two wavelengths selected to form the best ratio pair.

The ratio of the absorbance readings for the selected pair of wavelengths determined in step 126 is computed for the unknown sample, step 130. Then the regression coefficients contained in the mathematical correlation, determined during the training procedure and saved in step 127, are applied to the ratio obtained for the additional individual unknown blood sample 131, in order to yield the predicted hematocrit or hemoglobin concentration, step 132.

The ratio pre-processing technique serves to eliminate the variances of spectral data caused by scatter or other multiplicative errors in each of the various samples of both the training set and each unknown sample. This scatter would otherwise disrupt the accuracy of the detection of the training set spectra and its ability to predict the property in the unknown sample. Because both wavelengths in the selected best pair of wavelengths used in the ratio experience the same path length, variations in the effective path length due to scatter are minimized.

If the near infrared spectrum consists of N individual wavelengths, computing all possible ratios of each pair of wavelengths provides N*N new spectral features. In FIG. 2, such computation of all possible ratios is shown at step 123. The best possible ratio pair of wavelengths must be distilled from the myriad of combinations using regression mathematical techniques, as is shown in FIG. 2 at step 124, depicted in a correlation map at step 125, and selected at step 126 for use to determine the best possible regression coefficients in step 127 and for use with each unknown sample in step 130.

Any of a number of regression techniques; such as, linear regression, multiple linear regression, stepwise regression, partial least squares regression, or principal component regression can be used to develop a statistical correlation between the ratio spectral features and the variable of the property being quantified. Such regression techniques are available by reference to such literature as Draper and Smith, *Applied Regression Analysis*, Wiley and Sons, New York, 1982 and Geladi and Kowalski, *Analytica Chimica Acta*, Volume 185, pp 1–17 and 19–32, 1986, the disclosures of which are incorporated by reference herein.

In order to determine the best ratio for a given application, regression models are computed against all possible ratio pairs of wavelengths.

Each regression model is evaluated by using an accepted statistical measure. For example, one useful measure is the simple correlation coefficient computed from the actual hematocrit value obtained from the independent quantification and the predicted hematocrit value obtained from the regression model, as is shown in FIG. 2 at step 126.

A correlation map can be constructed to visually show which wavelength ratios provide the highest correlation, as is shown in FIG. 2, at step 125. A representative correlation map for hematocrit appears as FIG. 3 and a representative map for hemoglobin appears as FIG. 4. It is important to consider both high correlation and also the sensitivity of the correlation obtained to measure small changes in the actual wavelengths. The best overall ratio is found by selecting the pair of wavelengths which provide high correlation and which occur in a reasonably flat region of the correlation map.

Use of the spectral analytical instrumentation described above and depicted in FIG. 1 and the mathematical methods described above and depicted in FIG. 2 permit the analysis of the property of interest in the biological matter which contains water, so long as it is possible to develop a mathematical correlation between that property and water when establishing the training set through independent quantification of the property, spectra of the samples and use of ratio pre-processing techniques to minimize variability.

The determination of the mathematical correlation or model is founded on the linear functional relationship of the multiple linear regression equation: $B_0+B_1(A_1)+B_2(A_2)+\ldots B_n(A_n)=C$ where $B_0$ is the intercept, $B_n$ is the regression coefficient for the nth independent variable, $A_n$ is the nth independent variable and C is the value of the property of interest to be analyzed. Solving this equation depends upon the determination of regression coefficient(s) including the intercept and providing the values of the independent variable(s).

When the linear functional relationship is less complex, the equation is more often expressed as the linear regression equation: $Y=mx+b$ where Y is the value of the property of interest to be analyzed, m is the regression coefficient indicating the slope of the line, b is the intercept of the line and x is the single independent variable. Thus, the mathematical correlation endeavors to yield a linear relationship between the single independent variable, which is the ratio of the two best absorbance pairs, and the property of interest to be measured.

Once the mathematical correlation is established, it is validated. The accuracy in formation and performance is reviewed to assure reproducibility. The accuracy and the precision of the mathematical correlation can be validated by physical interpretation of the selected spectral features or using additional samples analyzed by independent quantification, step 121, and then subjecting those samples to steps 128 to 132 as if the samples were unknown. Statistical methods may then be used to compare the value of the predicted property, step 132, and the value determined by independent quantification, step 121, to confirm reproducibility.

One statistic standard error of calibration, measures precision of formation of the model of the training set, i.e., how well the regression analysis performs with the data used to construct the training set. The standard error of calibration (SEC) can be calculated from the following equation:

$$SEC = \left[ \frac{1}{N_T - n - 1} \sum_{i=1}^{N_T} (C_i - \hat{C}_i)^2 \right]^{1/2}$$

where $N_T$ is the number of training samples, n is the number of absorbance terms in the regression technique employed, $C_i$ is the hematocrit or hemoglobin value of the ith sample as calculated during linear regression and $\hat{C}_i$ is the hematocrit or hemoglobin value of the ith as independently determined. The smaller the SEC, the more precise the model mathematical correlation has been formed.

More importantly, another statistic, the standard error of prediction (SEP), measures the assurance of reproducible performance, i.e., a test to identify quantitatively the accuracy of the prediction results obtained using the method of the present invention with the actual value for the property determined by independent quantification using known and accepted techniques and may be used in conjunction with a confidence limit to quantitatively express the precision of the accuracy of the property being analyzed. Mathematically, the standard error of prediction can be calculated from the following equation:

$$SEP = \left[ \frac{1}{N_P - n - 1} \sum_{i=1}^{N_P} (C_i - \hat{C}_i)^2 \right]^{1/2}$$

where $N_P$ is the number of validation samples, $C_i$ is the independently quantified value for the ith validation sample, $C_i$ is the value for the ith validation sample obtained using the mathematical correlation of step 131. Also, the smaller the SEP, the more accurate and precise the prediction.

Bias measures the extent of deviation of all points within a given data set in the solved mathematical equation from the line of exact correlation between predicted and actual values. Qualitatively, a low bias indicates the presence of a robustness of the training set spectra to tolerate possible error. In other words, the robustness of the training set sampling anticipates the variety of sampling possibilities for the unknown sample and minimizes its effect.

Without being limited thereto or thereby, the following examples illustrate the methods of the present invention used to analyze hematocrit and hemoglobin in whole blood.

EXAMPLE 1

On five separate occasions, a number of whole blood samples were withdrawn from different individuals and subjected to NIR spectra irradiation using instrumentation described with reference to FIG. 1 to obtain the absorbance spectrum of each sample. Also, a blank reference spectrum was obtained using an empty cell. The diffusely transmitted light was gathered after traveling through the each sample in a cuvette 113. All of the measurements were taken at room temperature, which fluctuated randomly over a range of about 3 degrees C.

The individual sessions are identified in Table I below as sets A–E and the number of samples analyzed are identified as the number of spectra obtained, which varies from 36 to 45 samples per set.

Through the use of Coulter counting, the hematocrit for each of the five sets was expressed in Table I below as a range varying from as low as 17 percent to as high as 50 percent. Similarly, except with respect to set A for which no values were obtained, the hemoglobin concentration range in each of the sets was determined by cell lysing, reaction with cyanide, and spectral measurement of cyanomet hemoglobin. The range for sets B–E of hemoglobin was from about 6.7 to about 17.0 grams per deciliter (g/dL).

Table I below further identifies the correlation of hematocrit to hemoglobin which demonstrated correlation for the spectra obtained in each of the five sets.

TABLE I

Sets of Samples Spectrally Analyzed and Independent Quantification Ranges of Hematocrit and Hemoglobin

| Sets | No. of Spectra Obtained | Hematocrit Range (Vol %) | Hemoglobin Range (g/dL) | Hematocrit/ Hemoglobin Correlation |
|---|---|---|---|---|
| A | 36 | 17.6–45.1% | No Values | — |
| B | 45 | 20.7–45.5% | 7.3–15.7* | 0.994 |
| C | 40 | 18.9–41.7% | 6.7–14.1 | 0.992 |
| D | 42 | 23.0–50.2% | 7.7–17.0 | 0.993 |
| E | 43 | 20.7–49.4% | 7.3–16.1 | 0.994 |

*One hemoglobin value was unavailable, leaving 44 values to determine the range.

While 206 individual samples and spectra were obtained in five sets for this example, generally, it is possible to develop a training set with independent quantification from as few as 25 samples to as many as an infinite number of samples.

The purpose of establishing a training set for comparisons and prediction purposes is to attempt to anticipate sampling differences which may exist in various individuals at various times. In other words, the training set should be as broad as possible to include as many variances within each of the factors affecting the measurement of the property of interest.

Ideally, the training set includes samples that represent all of the different kinds of changes in the hematocrit and hemoglobin concentration over a full range of values likely to be encountered in an unknown sample as well as all of the other kinds of changes within each factor likely to affect blood sampling, e.g., temperature, amount of liquids, details of light scattering, presence of other components, and physiological condition of the patient.

Notwithstanding such ranges of hematocrit and hemoglobin in these sets, it was seen that the correlation between hematocrit and hemoglobin is quite precise, over 0.99 in all cases.

Having established training sets A–E and independently quantifying the hematocrit and hemoglobin ranges within each of those sets, the mathematical analysis depicted in FIG. 2 is now performed. First, the ratioing pre-processing technique was performed against each of the five sets. Using the following software routines written in Fortran and used with a computer, all possible ratios were computed, the linear regression was performed, the best ratio was selected, the regression coefficients were saved (steps 123, 124,126, and 127 of FIG. 2). Procedures in "VAX IDL Interactive Data Language" available from Research Systems Inc. (copyright 1982–1988) was used with a computer to perform the ratio pre-processing on the unknown sample, apply the regression model, and predict the property (steps 130, 131, and 132 of FIG. 2), and to compute the SEC, SEP, and bias for validation purposes.

Fortran Software Program (Complies with ANSI Fortran 77) Copyright, 1989, Minnesota Mining and Manufacturing Company

```
       REAL DATA(200,500),YVAL(200),TEMP(1500)
       REAL DOUT(500,500),NSPEC,NWAVE
       CHARACTER*30 FILEN
       WRITE (6, 100)
 100   FORMAT (' ENTER THE SPECTRAL DATA FILE
       NAME: ')
       READ (5, 101) FILEN
 101   FORMAT (A)
       OPEN (20, FILE=FILEN, STATUS='OLD',
       1FORM='UNFORMATTED', ERR=9999)
       READ (20) NSPEC, NWAVE
 10    WRITE (6,102)
 102   FORMAT (' ENTER SPACING BETWEEN SPECTRAL
       POINTS: ')
       READ (5,*) NSKIP
       IF (NWAVE/NSKIP .GT. 500) GOTO 10
       DO 20 I=1,NSPEC
       READ (20) (TEMP(J), J=1, NWAVE)
       DO 20 J=0,NWAVE/NSKIP-1
 20    DATA(I,J+1) = TEMP(NSKIP*J+1)
       CLOSE (20)
       WRITE (6, 103)
 103   FORMAT (' ENTER THE PROPERTY DATA
       FILE NAME: ')
       READ (5, 101) FILEN
       OPEN (20, FILE=FILEN, STATUS='OLD',
       1FORM='UNFORMATTED', ERR=9999)
       READ (20) NSPEC
       DO 30 I=1,NSPEC
 30    READ (20) YVAL(I)
       CLOSE (20)
       AVEY = YVAL(1)
       DO 40 I=2,NSPEC
 40    AVEY = AVEY + YVAL(I)
       AVEY = AVEY / NSPEC
       YFACT = 0.0
       DO 50 I = 1, NSPEC
```

-continued

```
 50  YFACT = YFACT + (YVAL(I)-AVEY)*(YVAL(I)-AVEY)
     IF (YFACT .LT. 1.0E-06) GO TO 9999
     ZCORR = 0.0
     DO 80 I=1,NWAVE/NSKIP
     DO 80 J=1,NWAVE/NSKIP
     AVEX=0.0
     DO 60 K=1,NSPEC
     TEMP(K) = DATA(K,J)/(DATA(K,I)+1.0E-6)
 60  AVEX = AVEX + TEMP(K)
     AVEX = AVEX / NSPEC
     XFACT = 0.0
     XYFACT = 0.0
     DO 70 K=1,NSPEC
     XFACT = XFACT + (TEMP(K)-AVEX)*(TEMP(K)-AVEX)
 70  XYFACT = XYFACT + (TEMP(K)-AVEX)*(YVAL(K)
     -AVEY)
     IF (ABS(XFACT) .LT. 1E-6) DOUT(J,I)=0.0
     IF (ABS(XFACT) .GE. 1E-6)
     1DOUT(J,I) = (XYFACT/XFACT)*(XYFACT/YFACT)
     IF (DOUT(J,I) .LE. ZCORR) GO TO 80
     ZCORR = DOUT(J,I)
     ZXCOL = J
     ZYCOL = I
     ZAVEX = AVEX
     ZXFACT = XFACT
     ZXY = XYFACT
 80  CONTINUE
     WRITE (6,104) INT(1+(ZXCOL-1)*NSKIP),
     INT(1+(ZYCOL-1)*NSKIP)
 104 FORMAT (/,' NUMERATOR WAVELENGTH: ',I4,
     1/,' DENOMINATOR WAVELENGTH: ',I4)
     SLOPE = ZXY/ZXFACT
     WRITE (6,105) ZCORR, SLOPE, AVEY-SLOPE*ZAVEX
 105 FORMAT (/,' CORRELATION COEFF.: ',1PE11.4,
     1/,' SLOPE: ',E10.3,/,' INTERCEPT: ',E10.3)
     WRITE (6,106)
 106 FORMAT (' ENTER THE OUTPUT FILE NAME: ')
     READ (5, 101) FILEN
     OPEN (20, FILE=FILEN, FORM='UNFORMATTED',
     STATUS='NEW')
     WRITE (20) NWAVE/NSKIP,NWAVE/NSKIP,0.0,0.0
     DO 90 I=1,NWAVE/NSKIP
 90  WRITE (20) (DOUT(J,I), J=1,NWAVE/NSKIP)
9999 CLOSE (20)
     STOP
     END
```

The ratioing pre-processing technique compared all possible combinations of wavelength pairs in order to find the best ratio relationship. Table II below identifies the best wavelength pairs found for each of the five sets, the corresponding multiple correlation coefficient for each set file models, and the slope and intercept regression coefficients.

TABLE II

| Sets | Ratio Pre-Processing Applied Against Each Spectral Data Set | | | |
|------|----------------|------------|--------|-----------|
|      | Ratio Wavelengths | Multiple R | Slope  | Intercept |
| A    | 1170 / 817 nm  | 0.951      | −226.4 | 224.2     |
| B    | 1170 / 813 nm  | 0.986      | −227.6 | 227.1     |
| C*   | 1196 / 1170 nm | 0.988      | 440.8  | −441.4    |
| D    | 1181 / 812 nm  | 0.979      | −310.2 | 301.3     |
| E    | 816 / 1169 nm  | 0.985      | 187.1  | −188.2    |

* It should be noted that the ratio pair at 817/1170 had nearly identical results to Sets A, B, D, and E with with a Multiple R value of about 0.986, a slope of 165.74, and an intercept of −162.15.

As may be seen, set C identified the best ratio of wavelengths to be two absorbance wavelengths very close to one another, whereas sets A, B, D, and E identify the best ratio wavelengths pairs to be in the range from about 810 to about 820 nm and from about 1169 to about 1181 nm. For these sets and under these instrumentation settings, the absorbances at about 810 to 825 nm correlated with the isosbestic point of oxyhemoglobin and deoxyhemoglobin, although the isosbestic point of oxyhemoglobin and deoxyhemoglobin has been reported variously in the literature to exist between about 780 to about 830 nm. The absorbances in the range from about 1150 to about 1190 nm, and particularly between 1150 and 1170 nm, conform to a strong absorbance peak for water. Thus, applying the ratio pre-processing technique variability was minimized when using ratios of wavelengths of the water content in blood with an absorbance of hemoglobin which minimized variability due to the oxygenated or deoxygenated state of the hemoglobin.

It is important to note that the multiple correlation coefficient for each of five data sets was at least 0.95, which permitted at least qualitative confirmation of the hypothesis that there is at least near linear correlation between the prediction of hematocrit and the actual values to be measured using more expensive, less rapid techniques.

EXAMPLE 2

The data in Table I were subjected to the same ratio pre-processing technique and analysis, using the same listed and VAX IDL software, as that used in Example 1, except that all five data sets A–E were combined for determining the ratio of the best wavelength pair. Such ratio pre-processing technique yielded a number of possibilities equal to the square of the number of spectral datapoints, and mathematical regression analysis such as that described with reference to FIG. 2 must be employed to determine the best pair of absorbance wavelengths for ratioing and to establish the mathematical correlation to which the unknown sample's spectra may be compared. The following mathematical correlation equation was derived to establish the training set for comparison of unknown samples of whole blood where hematocrit was desired to be measured:

$$\% \text{ Hematocrit} = -158.7 + 160.8 * (Abs_{820}/Abs_{1161})$$

The overall correlation coefficient for the combined sets A–E was 0.971 and standard error of calibration (SEC) was 1.62 percent. Thus, qualitatively, use of the combined sets A–E permits confirmation of the hypothesis of correlation of near linearity of relationship between analyzed values and actual values determined by other known methods. Further, quantitatively, the standard error established that the correlation was a good model for use in predicting unknown samples, i.e., within two percent of the actual values measured by a known method.

Figure 3:
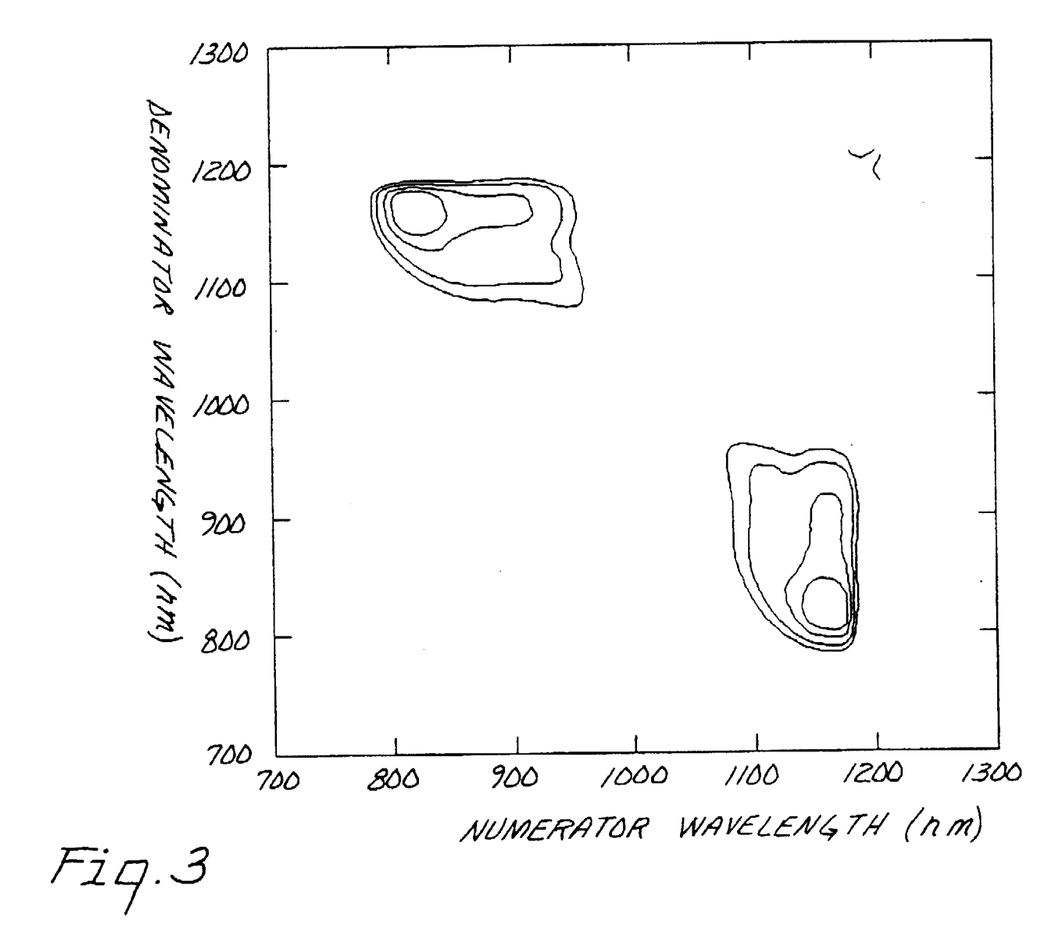
FIG. 3 is a graphic representation of a correlation map of correlation coefficient versus wavelength for hematocrit after ratio pre-processing and regression analysis of the spectral data was performed against hematocrit.

Graphically, the correlation of the wavelength pairs was developed using software available from Research Systems Inc., copyright 1982–1988 entitled "VAX IDL, Interactive Data Language" FIG. 3 identifies a correlation map which combined all datasets of this example and topographically measured the lines of equal correlation at 0.80, 0.85, 0.90, and 0.925 using the square of the multiple correlation coefficient for the various pairs of ratios determined by the pre-processing technique. The high degree of symmetry around the 45 degree axis of the graph in FIG. 3 implied that inverting the ratio of the pair of wavelengths provided similar results. This high degree of symmetry was be found in the results shown in Table II. Sets A, B, and D selected a ratio of water to hemoglobin; set E selected a ratio of hemoglobin to water.

In this example, two significant areas of correlation were observed, with the highest correlation occurring when the ratio of approximately 820 to 1160 nm is used. However, for circumstances where less accurate analysis was acceptable, the topographical regions indicated acceptance levels within the same tolerances as the lines record.

EXAMPLE 3

The same spectral data was used to compare with independent quantification of the concentration of hemoglobin. Because set A had no independent quantifications of hemoglobin, sets B–E were subjected to the same steps of analysis as for hematocrit in Examples 1 and 2. The analysis used the same listed software and the same VAX IDL software described above in Example 1. The result of the regression analysis to determine the best possible pair of wavelengths yielded 820 nm and 1153 nm, again in the areas of the isosbestic point of oxy and deoxy hemoglobin and the strong absorbance peak of water, respectively.

Table III identifies the sets, the selected ratio wavelengths, the multiple correlation coefficient, and the slope and intercept found for each set.

TABLE III

Ratio Pre-processing Applied Against Each Spectral Data Set for Hemoglobin

| Sets | Ratio Wavelengths | Multiple R | Slope | Intercept |
|---|---|---|---|---|
| B | 812/1165 | 0.976 | 56.16 | −54.98 |
| C | 804/1165 | 0.963 | 58.24 | −56.38 |
| D | 832/1161 | 0.957 | 56.15 | −56.97 |
| E | 816/1173 | 0.983 | 68.29 | −69.18 |

The mathematical correlation was developed:

$$\text{Concentration of Hemoglobin} = -57.78 + 57.61 * (Abs_{820}/Abs_{1153})$$

The overall correlation coefficient for the combined sets B–E was 0.9772 and the standard error of calibration (SEC) was 0.504 g/dL. Both results showed the presence of a model as accurate as the mathematical correlation for percent hematocrit of Example 2.

EXAMPLE 4

Figure 4:
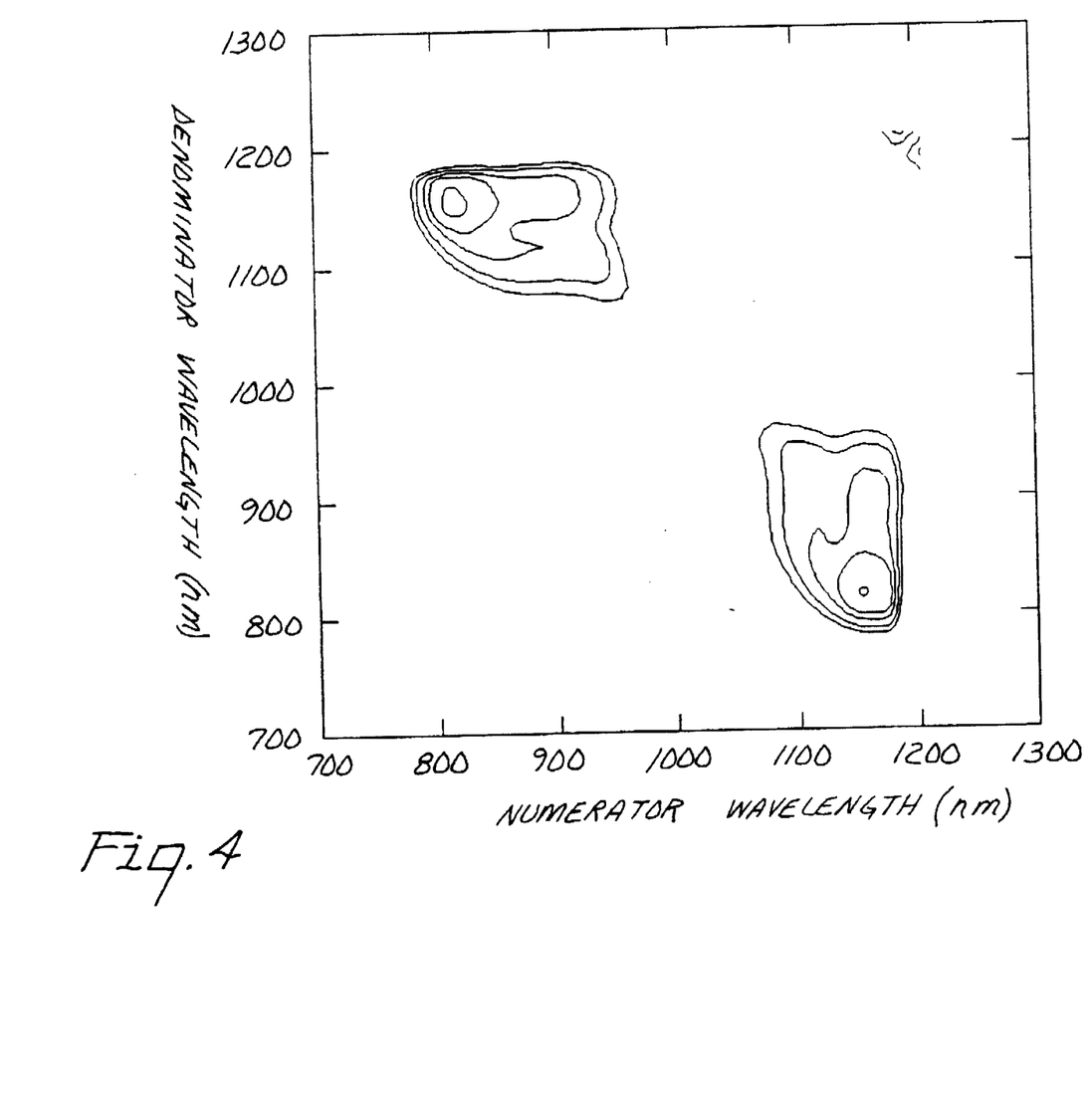
FIG. 4 is a graphic representation of a correlation map of correlation coefficient versus wavelength for hemoglobin after ratio pre-processing and regression analysis of the spectral data was performed against hematocrit.

Because of the deviation between the choice of the best wavelength pair between the hematocrit of Example 2 and the hemoglobin of Example 3, a second point on the correlation map graphed in FIG. 4 corresponding to the wavelength pair chosen in Example 2 for hematocrit was employed to determine hemoglobin. A procedure in the VAX IDL software described above was used to compute the slope and intercept using the previously identified wavelength pair. Thus, determining this mathematical correlation allowed the use of the same wavelength pair to determine both hemoglobin and hematocrit, if desired.

The mathematical correlation so determined was:

$$\text{Concentration of Hemoglobin} = -56.42 + 56.75 * (Abs_{820}/Abs_{1161})$$

The overall correlation coefficient was 0.9764 and the SEC was 0.514 g/dL. Both results showed the formation of a good model for prediction and as accurate as the models of Example 3. This was further evidence of the proper selection of these pairs of wavelengths in regions of broad plateaus of acceptable establishment of training sets.

FIG. 4 is a correlation map of concentration of hemoglobin at lines of equal correlation at 0.80, 0.85, 0.90, 0.925, and 0.950 using the squares of the multiple correlation coefficients obtained from Examples 3 and 4. An overlay of the maps of FIGS. 3 and 4 demonstrated the correlation of the hematocrit and concentration of hemoglobin using the methods of the present invention.

EXAMPLE 5

In order to simulate the prediction of an unknown sample, each of the five sets was treated as an unknown set and compared to the training set of the combination of all five data sets. The same mathematical equation described in Example 2 above and the same VAX IDL software described above in Example 1 were used to compute the results. Table IV below shows the results for predicting the hematocrit for each of the five data sets as compared with the combined data sets of all five.

TABLE IV

Ratio Pre-Processing Technique And Prediction Correlations For Each Set Against The Combination Of All Sets

| Sets | Multiple R | SEC | Bias |
|---|---|---|---|
| A | 0.947 | 2.29% | 0.86% |
| B | 0.986 | 1.16% | −0.35% |
| C | 0.967 | 1.11% | −0.63% |
| D | 0.977 | 1.88% | 0.87% |
| E | 0.985 | 1.74% | −0.72% |

As may be seen by comparing the results of the multiple correlation coefficient for each set in Tables II and IV, the correlation coefficients were very similar and in some cases identical.

The standard error of calibration (SEC) is within 2.3 percent, demonstrating quantitatively that correlation between predicted values and actual values measured by known methods yielded a correlation coefficient greater than 0.94 in all cases.

Here, the bias ranged from a −0.72 to 0.87 percent, demonstrating that variability due to instrumentation or sampling differences was nearly eliminated by use of the ratio pre-processing technique as described with reference to FIG. 2 on a robust number of training samples having a broad range of hematocrit percentages.

From this data, it was determined that the ratio pre-processing technique in combination with the regression mathematical analysis depicted in FIG. 2 establish an acceptable spectral analytical method for determining hematocrit.

EXAMPLE 6–7

As counterpoint to the prediction in Example 5 of the data of Example 2, these examples performed the same prediction for the two hemoglobin Examples 3 and 4 using the same equations and software as used in Examples 3 and 4, respectively. The results shown in Tables V and VI were comparable to hematocrit.

TABLE V

Ratio Pre-Processing Technique and Prediction Correlations for Each Set B–E Against The Combination of All Sets B–E at the Ratio of 820 nm to 1153 nm

| Sets | Multiple R | SEC(g/dL) | Bias(g/dL) |
|---|---|---|---|
| B | 0.9865 | 0.387 | 0.0711 |
| C | 0.9792 | 0.423 | −0.1166 |
| D | 0.9764 | 0.670 | 0.3343 |
| E | 0.9886 | 0.553 | −0.2936 |

TABLE VI

Ratio Pre-Processing Technique and
Prediction Correlations for Each Set B–E
Against the Combination of All Sets B–E
at the Ratio of 820 nm to 1161 nm

| Sets | Multiple R | SEC(g/dL) | Bias(g/dL) |
|---|---|---|---|
| B | 0.987 | 0.364 | –0.0072 |
| C | 0.980 | 0.433 | –0.1695 |
| D | 0.978 | 0.720 | 0.4374 |
| E | 0.991 | 0.537 | –0.2617 |

EXAMPLE 8

As further evidence of the ability of the method of the present invention to establish a source of spectral data for comparison with an unknown sample, each of the five sets was analyzed individually as training sets for the purposes of predicting some or all of the other sets simulated as unknown samples. The same ratio pre-processing technique and regression mathematical analysis as used for Examples 2 and 5, using the same VAX IDL software as used in Example 4, were employed in this Example. The equation used in each prediction was the ratio of absorbances at 820 nm and 1161 nm times the applicable slope, added to the applicable intercept as seen in Table VII below.

Table VII identifies the prediction results which demonstrates Standard Errors of Prediction as small as 2.6 percent and bias less than 1.65 percent. These results were a better indication than the results of Example 5 to demonstrate the ability of the method of the present invention to accurately predict hematocrit and hemoglobin in unknown whole blood because the data sets were segregated for the purposes of establishing the training set and simulating the unknown sampling.

TABLE VII

Ratio Pre-Processing Technique and Prediction
Correlations For Each Set As A Known Set Against
Other Set(s) As Unknown Samples–Hematocrit

| Known Set | Multiple R | SEC | Slope | Intercept | Unknown Set | SEP | Bias |
|---|---|---|---|---|---|---|---|
| A* | 0.947 | 2.09% | 153.49 | –150.74 | B | 1.60% | –1.14% |
|    |       |       |        |         | C | 1.61% | –1.27% |
|    |       |       |        |         | D | 1.76% | –0.04% |
|    |       |       |        |         | E | 2.40% | –1.58% |
| B  | 0.986 | 1.08% | 155.43 | –151.92 | A | 2.42% | 1.17% |
|    |       |       |        |         | C | 0.93% | –0.16% |
| C  | 0.987 | 0.90% | 159.65 | –156.72 | A | 2.59% | 1.45% |
|    |       |       |        |         | B | 1.12% | 0.25% |
| D  | 0.977 | 1.56% | 171.06 | –172.02 | E | 2.21% | –1.65% |
| E  | 0.984 | 1.33% | 180.97 | –182.33 | D | 2.15% | 1.71% |

Figure 5:
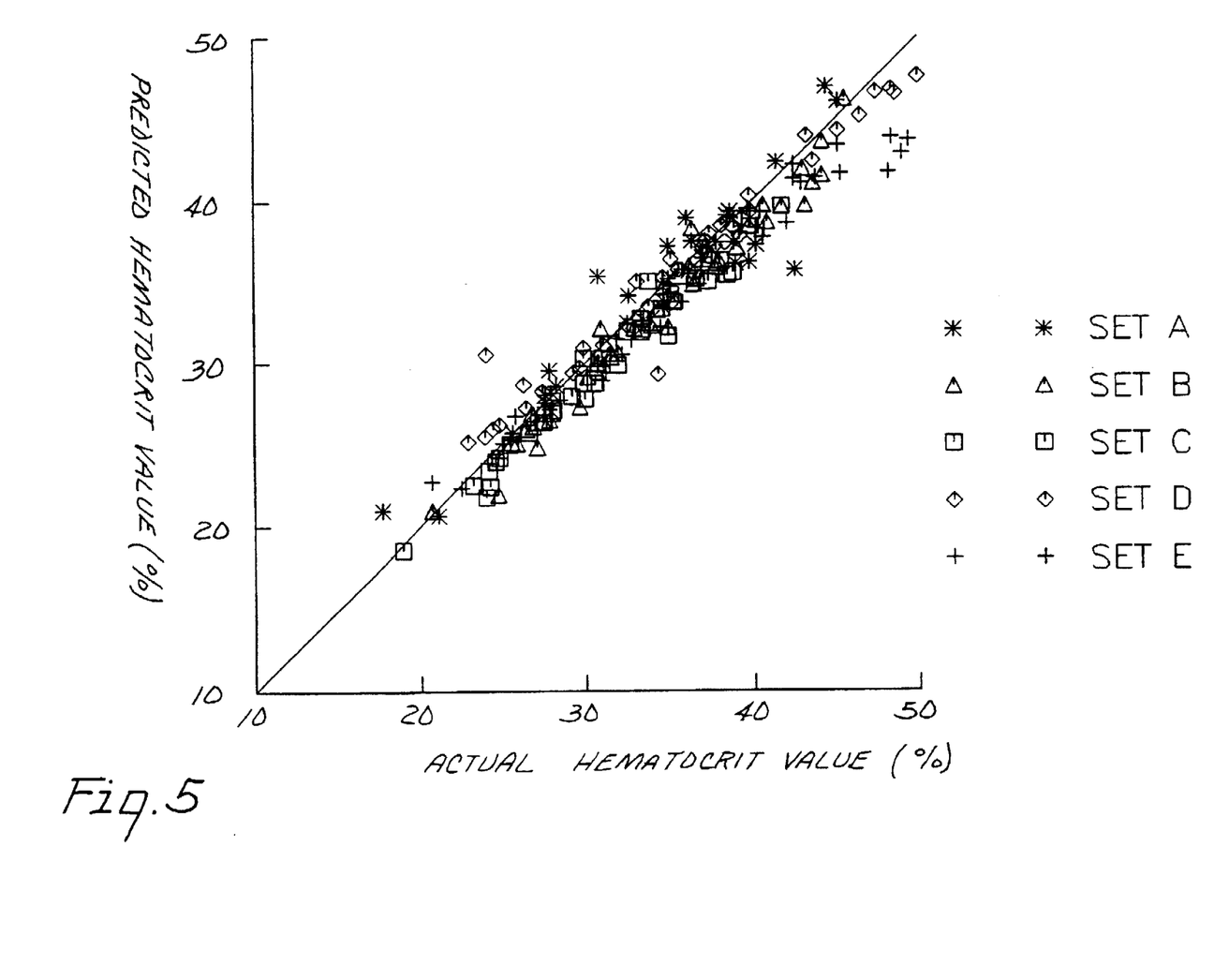
FIG. 5 is a graph showing the accuracy of prediction of hematocrit using the methods of the present invention compared with actual hematocrit determined by prior art methods.

* This set is graphically represented in FIG. 5.

The results of Example 8 seen in Table VII demonstrated the excellent ability of the ratio pre-processing technique and mathematical regression analysis to predict hematocrit in an unknown sample of blood. The SEP results demonstrated consistent accuracy within less than three percent, with any effect of bias as less than two percent either direction from linear correlation.

EXAMPLE 9–10

As further evidence of the ability of the method of the present invention to establish a source of spectral data for comparison with an unknown sample, each of sets B–E was analyzed individually as a training set for the purposes of predicting some or all of the other sets simulated as unknown samples. The same ratio pre-processing technique and regression mathematical analysis as used for Examples 3, 6 and 7, using the same VAX IDL software used in Example 4, were employed in these Examples. The equations used in the respective predictions were the applicable ratios of absorbances at 820 nm and either 1153 or 1161 nm, respectively, times the applicable slope, added to the applicable intercept as seen in Tables VIII and IX below.

Tables VIII and IX identify the prediction results which demonstrated Standard Errors of Prediction as small as less than one g/dL and bias less than 0.8 g/dL, regardless of whether the prediction was made using the 1153 nm ratio pair or the 1161 nm ratio pair. These results were a better indication than the results of Examples 6–7 to demonstrate the ability of the method of the present invention to accurately predict hemoglobin in unknown whole blood because the data sets were segregated for the purposes of establishing the training set and simulating the unknown sampling.

TABLE VIII

Ratio Pre-Processing Technique and Prediction
Correlations For Each Set As A Known Set Against
Other Set(s) As Unknown Samples–Hemoglobin
820/1153 Ratio Pair

| Known Set | Multiple R | SEC (g/dL) | Slope | Intercept | Unknown Set | SEP (g/dL) | Bias (g/dL) |
|---|---|---|---|---|---|---|---|
| B | 0.987 | 0.360 | 54.567 | –54.196 | C | 0.398 | –0.132 |
|   |       |       |        |         | D | 0.653 | 0.218 |
|   |       |       |        |         | E | 0.675 | –0.396 |
| C | 0.979 | 0.367 | 52.454 | –51.563 | B | 0.382 | 0.094 |
|   |       |       |        |         | D | 0.715 | 0.280 |
|   |       |       |        |         | E | 0.686 | –0.325 |
| D | 0.976 | 0.560 | 60.488 | –61.620 | B | 0.535 | –0.307 |
|   |       |       |        |         | C | 0.729 | –0.547 |
|   |       |       |        |         | E | 0.785 | –0.642 |
| E | 0.989 | 0.401 | 63.066 | –64.104 | B | 0.588 | 0.307 |
|   |       |       |        |         | C | 0.513 | 0.021 |
|   |       |       |        |         | D | 0.885 | 0.652 |

TABLE IX

Ratio Pre-Processing Technique and Prediction
Correlations For Each Set As A Known Set Against
Other Set(s) As Unknown Samples–Hemoglobin
820/1161 Ratio Pair

| Known Set | Multiple R | SEC (g/dL) | Slope | Intercept | Unknown Set | SEP (g/dL) | Bias (g/dL) |
|---|---|---|---|---|---|---|---|
| B | 0.987 | 0.354 | 54.602 | –53.848 | C | 0.391 | –0.123 |
|   |       |       |        |         | D | 0.721 | 0.406 |
|   |       |       |        |         | E | 0.599 | –0.281 |
| C | 0.980 | 0.356 | 51.752 | –50.371 | B | 0.379 | 0.073 |
|   |       |       |        |         | D | 0.776 | 0.426 |
|   |       |       |        |         | E | 0.664 | –0.244 |
| D | 0.978 | 0.546 | 59.524 | –60.225 | B | 0.654 | –0.496 |
|   |       |       |        |         | C | 0.860 | –0.708 |
|   |       |       |        |         | D | 0.843 | –0.715 |
| E | 0.991 | 0.363 | 63.709 | –64.562 | B | 0.536 | 0.168 |
|   |       |       |        |         | C | 0.557 | –0.120 |
|   |       |       |        |         | D | 0.959 | 0.740 |

Embodiments of the invention have been described using examples. However, it will be recognized that the scope of the invention is not to be limited thereto or thereby.

What is claimed is:

1. A method for analyzing a property of biological matter having a water content, the biological matter approximated to comprise a first compartment related to the property to be analyzed and a second compartment having a proportionally different amount of water than the first compartment, the method comprising:

(a) obtaining multiple samples of biological matter from at least one known organism of a given species;

(b) irradiating with near infrared light said multiple samples;

(c) detecting a near infrared spectrum of each of said multiple samples as spectral data consisting of absorbance intensities;

(d) applying a ratio pre-processing technique to the spectral data of absorbance intensities of the spectrum of each of said multiple samples to identify a multiplicity of ratio wavelength pairs;

(e) independently quantifying the property to be analyzed for each of said multiple samples;

(f) establishing a training set from said near infrared spectra from step (d) of said multiple samples using the multiplicity of ratio wavelength pairs;

(g) statistically identifying a nature of a best two compartment mathematical correlation between the property to be analyzed in the first compartment and the water content in the biological matter (1) by correlating values obtained during step (e) with values obtained during step (f) and (2) by selecting a ratio wavelength pair of absorbance intensities in which one wavelength is a near infrared wavelength absorbance peak of the water content and in which the second wavelength of the ratio wavelength pair is another near infrared wavelength absorbance measuring point having absorbances in the first compartment which minimize variability in the property to be analyzed;

(h) obtaining an unknown sample of biological matter from an organism of said given species;

(i) irradiating said unknown sample with near infrared light;

(j) detecting near infrared absorbance of said unknown sample at said near infrared wavelength absorbance peak of the water content and at said another near infrared wavelength absorbance measuring point as spectral data consisting of absorbance intensities;

(k) applying said ratio pre-processing technique using the ratio wavelength pair selected in step (g) to the spectral data of absorbance intensities of said near infrared absorbance peak of the water content and said another near infrared wavelength absorbance measuring point; and (l) predicting the property to be analyzed in said unknown sample by utilizing said best two compartment mathematical correlation obtained in said statistically identifying step (g).

2. The method according to claim 1, wherein said statistically identifying step (g) uses linear regression analysis.

3. The method according to claim 1, wherein said statistically identifying step (g) uses multiple linear regression analysis.

4. The method according to claim 1, wherein said statistically identifying step (g) uses stepwise regression analysis.

5. The method according to claim 1, wherein said statistically identifying step (g) uses partial least squares regression analysis.

6. The method according to claim 1, wherein the biological matter is whole blood and the property of the first compartment to be analyzed is hematocrit in whole blood.

7. The method according to claim 1, wherein the biological matter is whole blood and the property of the first compartment to be analyzed is hemoglobin concentration in the whole blood.

8. The method according to claim 1, wherein the biological matter is whole blood and said absorbance peak of water occurs in the near infrared spectra from about 1150 to about 1190 nanometers.

9. The method according to claim 1, wherein the biological matter is whole blood and said another absorbance measuring point is an isosbestic point of absorbance of oxyhemoglobin and deoxyhemoglobin.

10. The method according to claim 9, wherein said absorbance peak of water occurs in the near infrared spectra from about 1150 to about 1190 nanometers.

11. The method according to claim 10, wherein said mathematical correlation solves the equation:

$$Y = b + m*(\text{Absorbance at said Isosbestic Point/Absorbance of said Absorbance Peak of Water})$$

where Y is a value of hematocrit, b ranges from about −150 to about −183, and m ranges from about 153 to about 181.

12. The method according to claim 11, wherein said Absorbance Peak of Water ranges from about 1150 to about 1170 nm.

13. The method according to claim 10, wherein said mathematical correlation solves the equation:

$$Y = b + m*(\text{Absorbance at said Isosbestic Point/Absorbance of said Absorbance Peak of Water})$$

where Y is a concentration of hemoglobin, b ranges from about −50 to about −65, and m ranges from about 51 to about 64.

14. The method according to claim 13, wherein said Absorbance Peak of Water ranges from about 1150 to 1170 nm.

15. The method according to claim 1, wherein said detecting step (c) and said detecting step (j) use spectral analysis instrumentation which records the near infrared spectra of said multiple samples and said unknown sample in a static condition.

16. The method according to claim 15, wherein said detecting step (c) and said detecting step (j) use transmittance detection components in said spectral analysis instrumentation.

17. The method according to claim 15, wherein said detecting step (c) and said detecting step (j) use reflectance detection components in said spectral analysis instrumentation.

18. The method according to claim 1, further comprising between step (g) and step (h) the steps of:

(1) obtaining additional samples of biological matter from an organism of said given species;

(2) performing steps (b), (c), (d), (e) with respect to said additional samples;

(3) predicting the property to be analyzed in said additional samples by utilizing said mathematical correlation obtained in said statistically identifying step (g); and (4) validating said mathematical correlation by comparing the property predicted in step (3) to the property independently quantified in step (e).

19. The method according to claim 18, wherein said validating step (4) employs physical interpretation of the spectra of said additional samples compares to the training set.

20. The method according to claim 18, wherein said validating step (4) employs a statistical method to compare the property predicted in step (3) to the property independently quantified in step (e).

* * * * *